(12) United States Patent
Ying et al.

(10) Patent No.: US 10,718,012 B2
(45) Date of Patent: Jul. 21, 2020

(54) NON-MOTORIZED OPTICAL MULTIPLEXING FOR THE SIMULTANEOUS DETECTION OF DNA TARGET AMPLICONS IN A POLYMERASE CHAIN REACTION SOLUTION

(71) Applicant: AGENCY FOR SCIENCE, TECHNOLOGY AND RESEARCH, Singapore (SG)

(72) Inventors: Jackie Y. Ying, Singapore (SG); Saravana Kumar Kumarasamy, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 602 days.

(21) Appl. No.: 15/029,616

(22) PCT Filed: Oct. 14, 2014

(86) PCT No.: PCT/SG2014/000483
§ 371 (c)(1),
(2) Date: Apr. 14, 2016

(87) PCT Pub. No.: WO2015/057165
PCT Pub. Date: Apr. 23, 2015

(65) Prior Publication Data
US 2016/0230213 A1    Aug. 11, 2016

(30) Foreign Application Priority Data

Oct. 14, 2013  (SG) ................... 2013076500

(51) Int. Cl.
*G01J 5/60*    (2006.01)
*C12Q 1/686*    (2018.01)
*C12Q 1/6825*    (2018.01)

(52) U.S. Cl.
CPC .......... *C12Q 1/686* (2013.01); *C12Q 1/6825* (2013.01)

(58) Field of Classification Search
CPC ..................................................... C12Q 1/68
See application file for complete search history.

(56) References Cited

U.S. PATENT DOCUMENTS

| | | | | |
|---|---|---|---|---|
| 6,066,459 A | * | 5/2000 | Garini | C12Q 1/6841 435/6.1 |
| 2004/0191786 A1 | * | 9/2004 | Yue | G01N 33/542 435/6.18 |

(Continued)

OTHER PUBLICATIONS

Quorum, Possible Pitfalls of Using Multiband Emission Filters in Fluorescence Microscopy, attached, Jun. 2010.*

(Continued)

*Primary Examiner* — Aaron A Priest
(74) *Attorney, Agent, or Firm* — Womble Bond Dickinson (US) LLP

(57) ABSTRACT

A multiplexed polymerase chain reaction (PCR) DNA detection system and a method for DNA detection within the PCR system are provided. The PCR DNA detection system includes a color charge-coupled device (CCD) camera, fluorophore-quencher probes and an imaging chamber. The fluorophore-quencher probes are selected in response to fluorophores quenched by the fluorophore-quencher probes corresponding to three selected primary colors and peak channel responses of the CCD camera such that emission profiles of the fluorophores substantially match the three selected primary colors and peak emission profiles of the fluorophores correspond to the peak RGB channel responses of the CCD camera. A DNA sample and the fluorophore-quencher probes are located within the imaging chamber. The color CCD camera is focused on the imaging chamber for simultaneous detection of up to three targets from (Continued)

fluorescence of the DNA sample and the fluorophore-quencher probes.

11 Claims, 14 Drawing Sheets

(56) References Cited

U.S. PATENT DOCUMENTS

| | | | |
|---|---|---|---|
| 2005/0196760 A1* | 9/2005 | Pemov | C12Q 1/6825 435/6.11 |
| 2006/0269922 A1 | 11/2006 | Sagner et al. | |
| 2009/0201577 A1* | 8/2009 | LaPlante | G01N 21/6458 359/355 |
| 2010/0008862 A1* | 1/2010 | Fu | A61K 49/0002 424/9.32 |
| 2010/0015611 A1 | 1/2010 | Webster et al. | |
| 2011/0008785 A1* | 1/2011 | Tan | B01L 7/52 435/6.12 |
| 2012/0014835 A1 | 1/2012 | Howell et al. | |
| 2012/0171684 A1* | 7/2012 | Benson | C09B 15/00 435/6.12 |
| 2013/0261019 A1* | 10/2013 | Lin | C12Q 1/6825 506/9 |
| 2015/0346097 A1* | 12/2015 | Battrell | G01N 21/6428 435/6.11 |

OTHER PUBLICATIONS

Chroma (Multiband Filter Set, attached Jan. 18, 2011).*
Lee et al., Development of a CCD-based fluorimeter for real-time PCR machine, Sensors and Actuators B: Chemical vol. 107, Issue 2, Jun. 29, 2005, pp. 872-881.*
PCT Notification of Transmittal of the International Search Report and the Written Opinion of the International Searching Authority, or the Declaration for counterpart PCT Application No. PCT/SG2014/000483, 12 pp., (Dec. 22, 2014).
PCT International Preliminary Report on Patentability Counterpart Application No. PCT/SG2014/000483 (dated Oct. 14, 2014); 8 pages.
Mullis, K., et al. Specific enzymatic amplification of DNA in vitro: The polymerase chain reaction. Cold Spring Harb Symp Quant Biol 51, 263-273 (1986); 11 pp.
Higuchi, R., Dollinger, G., Walsh, P.S. & Griffith, R. Simultaneous amplification and detection of specific DNA sequences. Biotechnology 10, 413-417 (1992), 4 pp.
Chappell, D. Fundamentals of Real Time RT-PCR. Applied Biosystems, Inc., Foster City, CA, U.S.A., (2007); 79 pp.
Soundiram, I. GeneXpert Technology. Cepheid, Sunnyvale, CA, U.S.A., (2012); 30 pp.
Stevenson, W., "Idaho Technology, Inc. Seeks FDA clearance for the expanded FilmArray Respiratory Panel," Jan. 30, 2012 (1 page).
Greenwood, D.P., Jeys, T.H., Johnson, B., Richardson, J.M. & Shatz, M.P. Optical techniques for detecting and identifying biological-warfare agents. Proceed IEEE 97, 971-989 (2009); 20 pp.
Xu, G., et al. A self-contained all-in-one cartridge for sample preparation and real-time PCR in rapid influenza diagnosis. Lab Chip 10, 3103-3111 (2010); 4 pp.
Xiang, Q., Xu, B. & Li, D. Miniature real time PCR on chip with multi-channel fiber optical fluorescence detection module. Biomed Microdevices 9, 443-449 (2007); 7pp.
Lee, D.-S., el al. A novel real-time PCR machine with a miniature spectrometer for fluorescence sensing in a micro liter volume glass capillary. Sens Actuators B 100, 401-410 (2004) 10 pp.
Schabmueller, C.G.J., et al. Integrated diode detector and optical fibres for in situ detection within micromachined polymerase chain reaction chips. J Micromech Microeng 11, 329-333 (2001); 6 pp.
Geffen, N. Gene Xpert demonstrates good sensitivity and specificity but at high cost. 41st Union World Conference on Lung Health, Berlin, Germany, (2010); 5 pp.
Osborn, D. Filters for FISH imaging. Inmmunohistochemical Staining Methods eds. Kumar, G.L. & Rudbeck, L. Dako North America, Carpinteria. CA, U.S.A., (2009); 6 pp.
Lee, D.D. & Seung, H.S. Algorithms for non-negative matrix factorization. Adv Neural Info Proc Syst 13, 556-562, (2001); 7 pp.
Brunet, J.P., Tamayo, P., Golub, T.R. & Mesirov, J.P. Metagenes and molecular pattern discovery using matrix factorization. Proc Natl Acad Sci USA 101, 4164-4169 (2004); 6 pp.
Newberg, J. & Murphy, R.F. A framework for the automated analysis of subcellular patterns in human protein atlas images J Proteome Res 7, 2300-2308. (2008); 9 pp.
Macenko, M., et al. A method for normalizing histology slides for quantitative analysis. In IEEE International Symposium on Biomedical Imaging: From Nano to Macro, Boston, MA, U.S.A., (2009), 4 pp.
Ruifrok, A.C. & Johnston, D.A. Quantification of histochemical staining by color deconvolution. Anal Quant Cytol Histol 23, 291-299 (2001); 9 pp.
Biofire: "Identifying Respiratory Pathogens has never been easier"; Sep. 8, 2012; http://www.biofiredx.com/FilmArray/index.html; 1 pp.
Biofire: "Setting Up the FilmArray is Easy"; Sep. 5, 2012; http://www.biofiredx.com/FilmArray/HowitWroks.html, 1 pp.

* cited by examiner

400

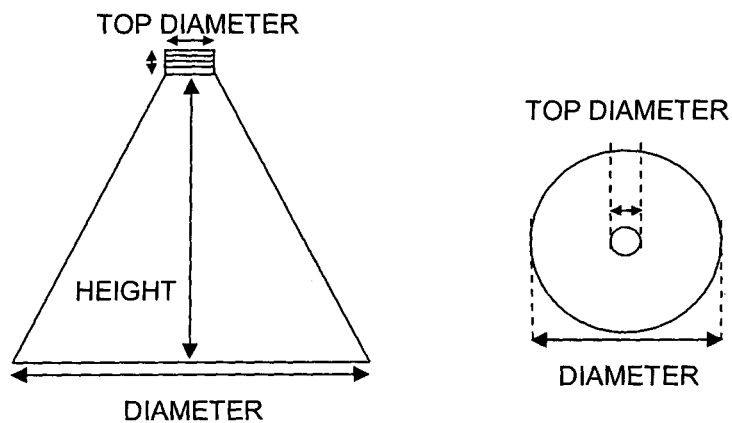
700
FIG. 7A
710
FIG. 7B
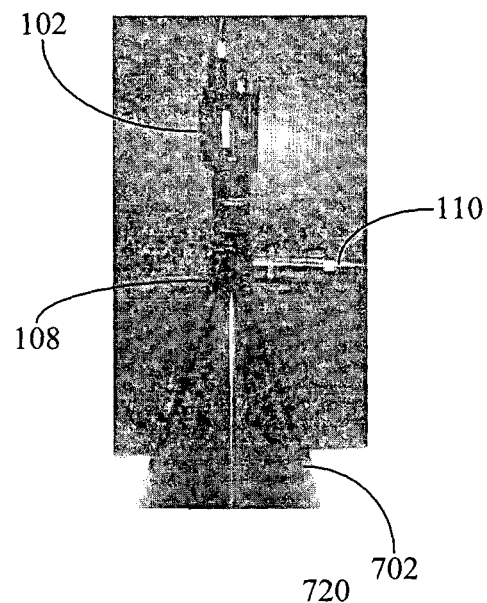
720
FIG. 7C

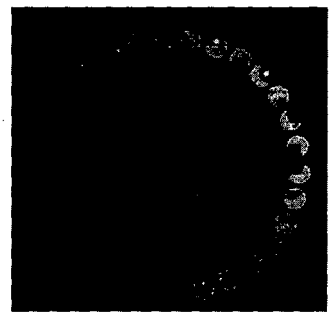
800
FIG. 8A
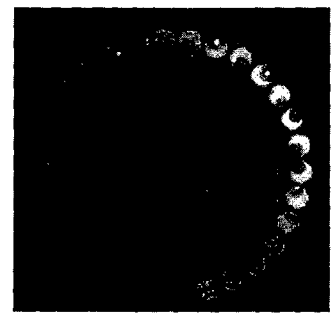
810
FIG. 8B
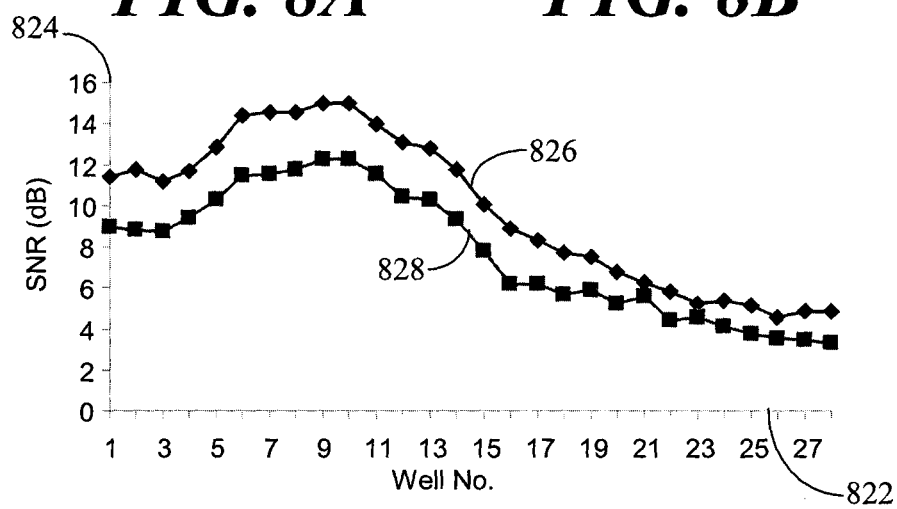
820
FIG. 8C
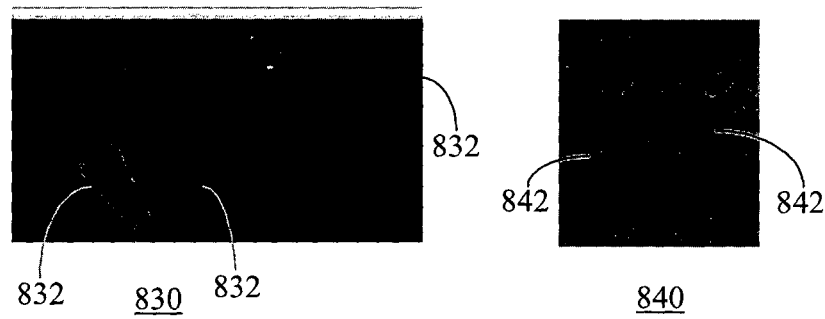
830     840
FIG. 8D     FIG. 8E

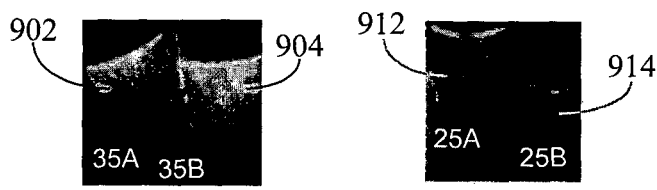
FIG. 9A  FIG. 9B
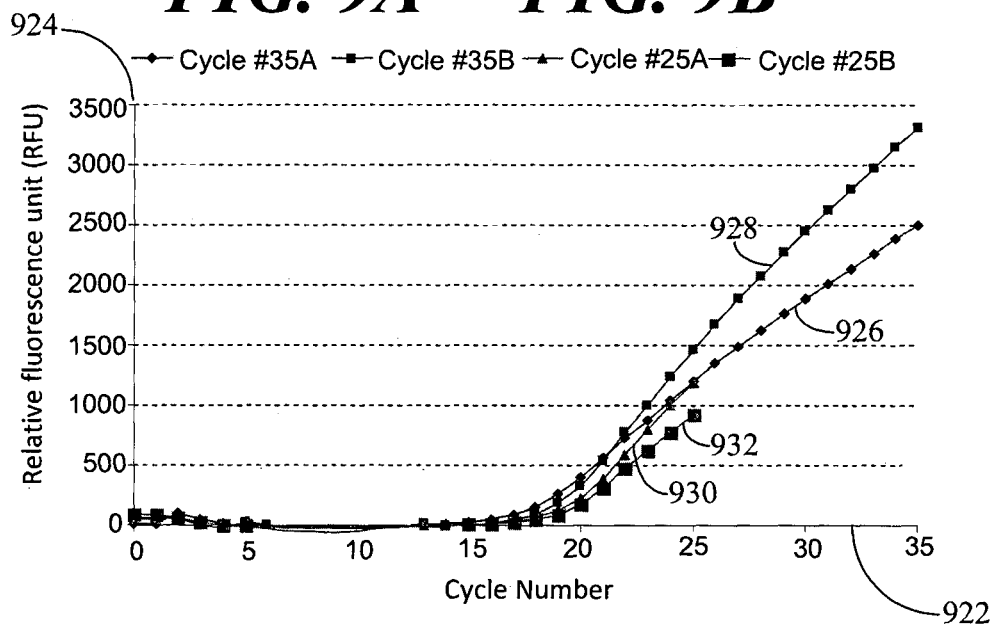
FIG. 9C
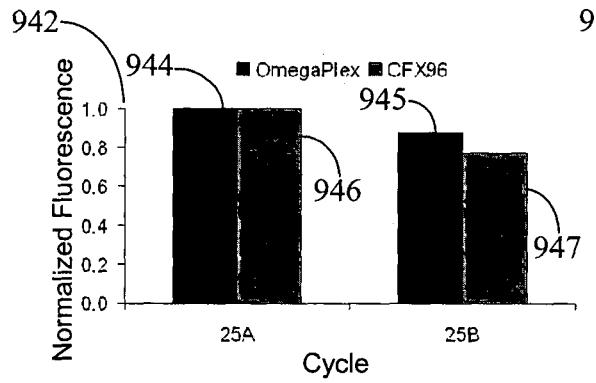 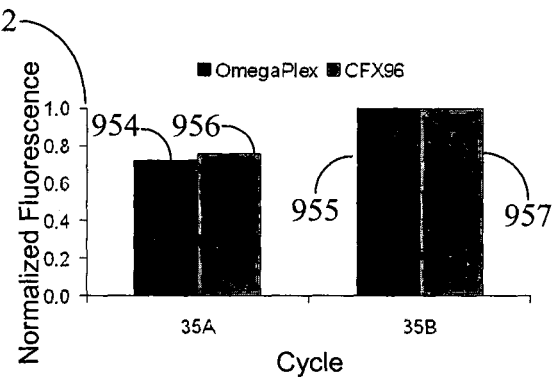
FIG. 9D  FIG. 9E

1200

1220

NON-MOTORIZED OPTICAL MULTIPLEXING FOR THE SIMULTANEOUS DETECTION OF DNA TARGET AMPLICONS IN A POLYMERASE CHAIN REACTION SOLUTION

CROSS-REFERENCE TO RELATED APPLICATIONS

The present application is a U.S. National Phase Application under 35 U.S.C. § 371 of International Application No. PCT/SG2014/000483, filed Oct. 14, 2014, entitled NON-MOTORIZED OPTICAL MULTIPLEXING FOR THE SIMULTANEOUS DETECTION OF DNA TARGET AMPLICONS IN A POLYMERASE CHAIN REACTION SOLUTION, which claims priority to Singapore Patent Application No. 201307650-0, filed Oct. 14, 2013.

FIELD OF THE INVENTION

The present invention relates to polymerase chain reaction (PCR) biological assay. In particular, it relates to non-motorized optical multiplexing for simultaneous detection of DNA target amplicons in a PCR solution.

BACKGROUND OF THE DISCLOSURE

Over the last thirty years, polymerase chain reaction (PCR) has become a widely used biological assay in both laboratory and clinical settings. Subsequently, the advent of real-time PCR enabled the automation of both the amplification and detection steps. Various bench-top real-time PCR devices with high-throughput and multiplexing features have been developed. More recently, fully automated systems that cover sample preparation, DNA extraction, PCR amplification and detection have also been developed. These devices enable the rapid, accurate and specific diagnosis of a host of bacterial and viral pathogens.

However, there is an acute and unmet need for such point-of-care (POC) diagnosis in developing countries where centralized laboratories are lacking. Portability is a key POC feature for PCR devices and would impact the design of optical modules for such systems. A portable system would require the optical module to (i) have non-movable components, (ii) occupy a smaller footprint, (iii) be battery operated, (iv) have sufficient detection sensitivity, and (v) provide moderate throughput and multiplexing.

Bench-top PCR devices designed for centralized laboratories usually employ movable optical components so that the detector (e.g. charge-coupled devices (CCDs), photo-multiplier tubes (PMTs), photodiodes) and excitation light source can be automatically positioned over different regions of a 96- or 384-well plate using an x-y motor. Bench-top PCR devices also employ motorized excitation, dichroic and emission filter wheels to automate the detection of multiple probes of specific spectral bandwidths.

However, the absence of an x-y motor would imply that the photodetector has a field of view as large as a 96- or 384-well plate. Also, the excitation light would need to be projected over a large area and, as such, the intensity of light per unit area must be sufficiently high to detect the fluorescent probes. This necessitates the use of high-powered tungsten or mercury lamps, which would detract from the goal of developing a portable POC PCR device. With the advent of high-power (greater than five watts), high brightness and compact light-emitting diode (LED) light sources in both ultraviolet (UV) and visible ranges of wavelengths, an efficient and battery-powered (approximately twelve volts) alternative to conventional light sources has been presented.

Further, different strategies have been implemented in developing a non-motorized optical detection system. For example, a single blue LED has been utilized to simultaneously excite fluorescence-conjugated probes with emission wavelengths of 530, 640 and 705 nm by fluorescence resonance energy transfer (FRET). The emission spectrum is then collected by three corresponding photodiodes via a cascade of emission bandpass filters and beam splitters. While this optical scheme is inexpensive, the collection efficiency of the emitted signal is limited to ~40-50% due to transmission losses.

One conventional solution proposed the use of a spectrometer for detecting and resolving emission wavelengths of fluorescence-conjugated DNA probes. The benefit of using a spectrometer is that it offers excellent wavelength resolution that is of importance in a multiplexed PCR setting. However, it lacks spatial resolution, and this necessitates the use of a motorized carousel to sequentially position the DNA samples in direct view of the optical fiber connected to the spectrometer. Alternatively, a 1- or 2-dimensional scanner needs to be incorporated to achieve spatial resolution.

Another conventional solution developed a CCD-based fluorimeter for real-time PCR. A 470-nm LED was used as an excitation light source, but instead of cascading the emission filters, a rotating disk was implemented with six optical filters to provide six fluorescence detection channels at 530, 560, 610, 640, 670 and 710 nm. Although the issue of limited collection efficiency is addressed, this design is more complex given the need to motorize the rotating disk.

A further conventional device utilizes a compact and modularized cartridge system comprising a PCR reaction chamber, a thermal cycling module, four LED excitation lights and corresponding photodiodes for detection. However, each cartridge processes only one patient sample and has a high cost. In addition, the integrated cartridge limits the scope of multiplexing to just optical, rather than a combination of spatial and optical multiplexing.

An additional solution implemented a real-time PCR optical detection system incorporating a laser, a filter cube, a photo-detector and a 1×4 fiber optical switch so that the fluorescence signal can be acquired from four different reaction sites. Such a design appears well-suited for a portable PCR system, whereby there is a spatial multiplexing of four and the entire system does not have any movable parts. However, there is no optical multiplexing since the laser produces excitation at a specific wavelength, and both the dichroic mirror and emission filter have bandpass properties.

A further system employs a real-time PCR device that uses a nested PCR, whereby amplified DNA samples are delivered to a multi-well chip for a second round of real-time PCR amplification. Each well is preloaded with a specific primer pair and SYBR green intercalating dye for the detection of a single DNA target using a non-movable CCD-based fluorescence imaging system. Although this system offers high spatial multiplexing, it has only a single optical channel for detection.

Thus, what is needed is a portable system with an optical module to (i) have non-movable components, (ii) occupy a smaller footprint, (iii) be battery operated, (iv) have sufficient detection sensitivity, and (v) provide moderate throughput and multiplexing. Furthermore, other desirable features and characteristics will become apparent from the subsequent detailed description and the appended claims, taken in conjunction with the accompanying drawings and this background of the disclosure.

SUMMARY

According to the Detailed Description, a multiplexed polymerase chain reaction (PCR) DNA detection system is provided. The PCR DNA detection system includes a color charge-coupled device (CCD) camera, fluorophore-quencher probes and an imaging chamber. The fluorophore-quencher probes are selected in response to fluorophores quenched by the fluorophore-quencher probes corresponding to three selected primary colors and peak channel responses of the CCD camera such that emission profiles of the fluorophores substantially match the three selected primary colors and peak emission profiles of the fluorophores correspond to the peak RGB channel responses of the CCD camera. A DNA sample and the fluorophore-quencher probes are located within the imaging chamber. The color CCD camera is focused on the imaging chamber for simultaneous detection of up to three targets from fluorescence of the DNA sample and the fluorophore-quencher probes.

In accordance with another aspect, a method for PCR detection in a system comprising a CCD camera is provided. The method includes optically multiplexing up to three targets with fluorophore-quencher probes. The fluorophore-quencher probes are selected in response to fluorophores quenched by the fluorophore-quencher probes corresponding to three selected primary colors and peak channel responses of the CCD camera such that emission profiles of the fluorophores substantially match the three selected primary colors and peak emission profiles of the fluorophores correspond to the peak RGB channel responses of the CCD camera.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present embodiment.

FIG. 6, comprising FIGS. 6A and 6B, illustrate RGB fluorophores in accordance with the present embodiment, wherein FIG. 6A illustrates the RGB fluorophores in a linear probe configuration and FIG. 6B illustrates the RGB fluorophores in a hairpin probe configuration.

FIG. 7, comprising FIGS. 7A, 7B and 7C, illustrates a light insulator of the PCR system of FIG. 1 in accordance with the present embodiment, wherein FIG. 7A is a front planar schematic view of the light insulator, FIG. 7B is a top planar schematic view of the light insulator, and FIG. 7C illustrates an optical system of the PCR system of FIG. 1 which incorporates the light insulator.

FIG. 8, comprising FIGS. 8A, 8B, 8C, 8D and 8E, illustrates a comparison between a glossy black surfaced substrate material and an aluminum sheet substrate material on the signal-to-noise ratio (SNR) of the fluorescence read-out from DNA probes in accordance with the present embodiment, wherein FIG. 8A depicts a FAM? probe in a multi-well DNA chip placed on a glossy black surface, FIG. 8B depicts a FAM? probe in a multi-well DNA chip placed on an aluminum sheet, FIG. 8C depicts a graph of the SNR of fluorescence read-out from each well in the DNA chip placed on the glossy black surface and the aluminum sheet, FIG. 8D depicts serial dilutions of a UV probe in PCR reaction tubes placed on a glossy black surface, and FIG. 8E depicts a UV probe in PCR reaction tubes placed on an aluminum sheet.

FIG. 9, comprising FIGS. 9A, 9B, 9C, 9D and 9E, illustrates a correlation between fluorescence read-out of a conventional real-time PCR system and the real-time PCR system of FIG. 1 in accordance with the present embodiment, wherein FIG. 9A depicts duplicate real-time PCR fluorescence read-out of the glyceraldehyde 3-phosphate dehydrogenase (GAPDH) mouse control gene using a fluorescein amidite Bull-Hutchings-Quayle probe (e.g., FAM-BHQ1 probe) after thirty-five cycles, FIG. 9B depicts duplicate real-time PCR fluorescence read-out of the GAPDH mouse control gene using a FAM-BHQ1 probe after twenty-five cycles, FIG. 9C depicts a graph of the PCR amplification results of the duplicate read-outs of each cycle of the cycles of FIGS. 9A and 9B using the real-time PCR system of FIG. 1 as compared to similar read-outs of each cycle of a conventional real-rime PCR system, FIG. 9D depicts a bar graph of normalized fluorescence read-out of the real-time PCR system of FIG. 1 and the conventional PCR system using the probes of FIG. 9B and correlated after twenty-five cycles, and FIG. 9E depicts a bar graph of normalized fluorescence read-out of the two PCR systems using the probes of FIG. 9A and correlated after thirty-five cycles FIG. 10, comprising FIGS. 10A, 10B, 10C and 10D, illustrates resolution of Cy3 and Cy5 fluorescence in a PCR solution using a conventional PCR system and the PCR system of FIG. 1 in accordance with the present embodiment, wherein FIG. 10A depicts a graph illustrating a three-plex real-time PCR amplification of GAPDH, β-actin and B2M mouse control genes using FAM-, Cy3- and Cy5-conjugated DNA probes with the conventional PCR system, FIG. 10B depicts end-point single-plex amplification results of FAM-GAPDH, Cy3-β-actin and Cy5-B2M, FIG. 10C depicts end-point duplex amplification results, and FIG. 10D depicts a RGB scatter plot of the amplification results of FIG. 10C.

FIG. 12, comprising FIGS. 12A and 12B, illustrates end-point PCR amplification results of GAPDH, B2M and β-actin mouse control genes using FAM, Cy5 and Alexa 405 probes, wherein FIG. 12A depicts single-plex reactions of FAM, Cy5 and Alexa 405 and FIG. 12B depicts duplex reactions of FAM+Alexa 405, FAM+Cy5 and Alexa 405+Cy5.

Skilled artisans will appreciate that elements in the figures are illustrated for simplicity and clarity and have not necessarily been depicted to scale. For example, the dimensions of some of the elements in the illustrations, block diagrams or flowcharts may be exaggerated in respect to other elements to help to improve understanding of the present embodiments.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of present embodiments to present an entirely static optical detection system for real-time PCR which provides a portable, point-of-care (POC) PCR system for diagnosis in developing countries where centralized laboratories are lacking. The portable real-time PCR system advantageously has an optical module with (i) non-movable components, (ii) a small footprint, (iii) battery operation, (iv) sufficient detection sensitivity, and (v) moderate throughput and multiplexing. Further, the real-time PCR system is a multiplexed DNA detection system that includes a color charge-coupled device (CCD) camera, fluorophore-quencher probes and an imaging chamber. The fluorophore-quencher probes are selected in response to fluorophores quenched by the fluorophore-quencher probes corresponding to three selected primary colors and peak channel responses of the CCD camera such that emission profiles of the fluorophores substantially match the three selected primary colors and peak emission profiles of the fluorophores correspond to the peak RGB channel responses of the CCD camera. A DNA sample and the fluorophore-quencher probes are located in the imaging chamber and the color CCD camera is focused on the imaging chamber for simultaneous detection of up to three targets from fluorescence of the DNA sample and the fluorophore-quencher probes.

Figure 1:
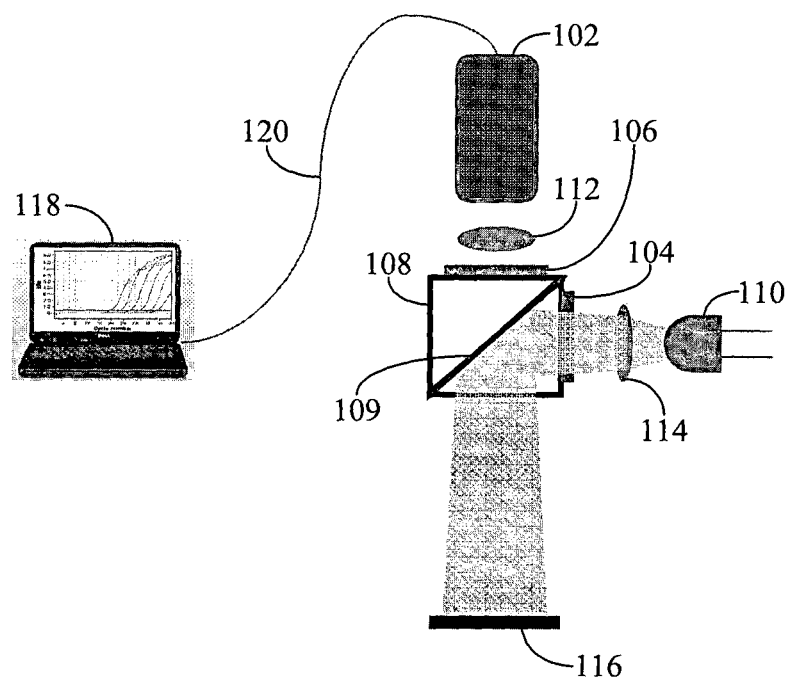
FIG. 1 illustrates a polymerase chain reaction (PCR) system in accordance with a present embodiment.

Referring to FIG. 1, a PCR system 100 in accordance with a present embodiment includes a color CCD camera 102, a full multiband excitation filter 104, a full multiband emission filter 106, a full multiband dichroic filter cube 108 with a dichroic mirror 109, a light source 110, collimating and focusing lenses 112, 114, a light-tight imaging chamber 116, and a computer 118. The computer 118 is coupled to the color CCD camera 102 by a cable 120, such as a firewire cable, and includes dedicated image processing software. The light source 110 is a broadband UV-visible (e.g., visible in the range of 380-700 nm wavelength) light source that can be implemented using a mercury lamp or light-emitting diode (LED) with a fiber optic cable.

The color CCD camera 102 covers a reasonably large field of view (e.g., approximately 15 cm×15 cm), whereas the multiband filters 104, 106, 108 enable the multiplexed detection of three primary colors from fluorophores tagging DNA probes in the imaging chamber 116. The fluorescence image is captured by the camera 102. Color-based deconvolution is then employed by the software in the computer 118 on the pixels in the PCR reaction to resolve fluorescence from a mixture of two or more DNA targets into its fluorophore components.

The fluorophores are chosen such that their emission profiles closely match the three primary colors red, green and blue (RGB). In accordance with the present embodiment, the DNA fluorescence probes can be selected from Alexa 405, Cascade Blue or Pacific Blue for blue emission profiles, Alexa 488, fluorescein amidite (FAM) or fluorescein isothyocyanate (FITC) for green emission profiles, and Texas Red, Cy5 or Alexa 647. Preferably, the DNA fluorescence probes in accordance with the present embodiment are Alexa 405, Alexa 488 and Texas Red. Non-motorized optical multiplexing is implemented by the use of these DNA fluorescence probes, the corresponding excitation of these fluorophores using the UV-visible light source 110 and the detection using a full tri-band filter set (excitation filter 104, emission filter 106 and dichroic filter cube 108) together with the RGB camera 102 controlled in real time by the customized image analysis software on the computer 118 via a firewire cable 120.

The optical system 100 can be broadly divided into four modules: (i) the UV-visible broad band mercury or LED light source 110, (ii) the excitation, emission and dichroic filters 104, 106, 108 (e.g., filters sold by Semrock Inc. of Rochester, N.Y., U.S.A.), each having compatible triple wavelength bands, (iii) the CCD-based RGB camera 102 and lens 112 (e.g., a Grasshopper2 CCD-based RGB camera with a 25-mm focus lens sold by Point Grey Research Inc. of Richmond, British Columbia, Canada), and (iv) customized image analysis software operating on the computer 118 to analyze images from the camera 102 (e.g., software developed using Matlab Image Acquisition Toolbox sold/licensed by The Mathworks Inc. of Natick, Mass., U.S.A.).

Figure 2:
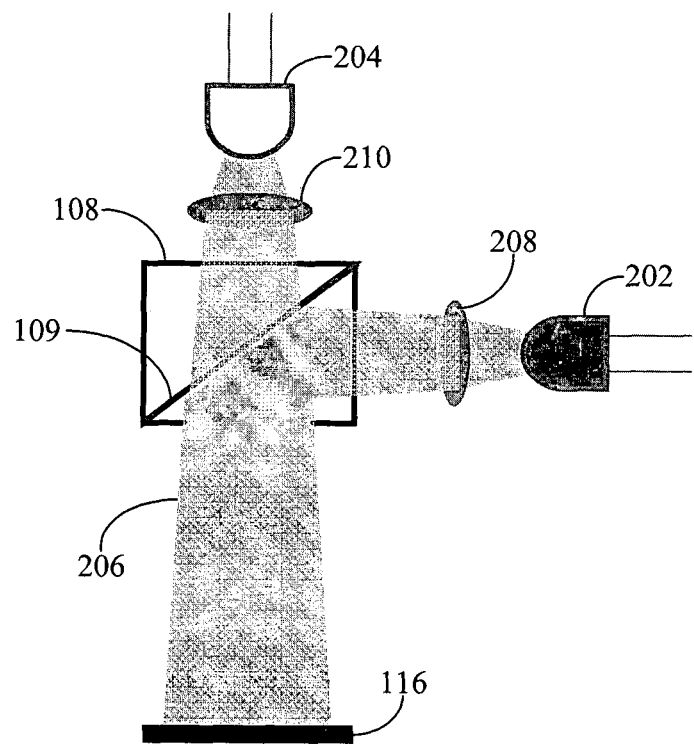
FIG. 2 illustrates a light emitting diode (LED) light source in the PCR system of FIG. 1 in accordance with the present embodiment.

The light source 110 can be implemented using a mercury light source (e.g., such as an EL6000 mercury light sold by Leica Microsystems of Wetzlar, Germany). An alternative light source arrangement 200 is shown in FIG. 2. In the light source arrangement 200, a combination of a UV LED 202 and a warm white visible LED 204 is used as the light source 110. The LEDs 202, 204 having a power rating greater than five watts can advantageously provide the optical system 100 with a broadband UV spectrum of 380-700 nm. In accordance with the present embodiment, the light source arrangement 200 is portable as it can be powered by a twelve volt battery and is advantageously equipped with a heat sink and a mini-fan (e.g., such as a five volt mini fan) for efficient heat removal.

The dichroic mirror 109 in the filter cube 108 reflects light from the UV LED 202, and transmits light from the visible white LED 204, so that a UV visible light beam 206 is incident on the DNA sample in the image chamber 116, the light beam 206 being a UV-visible broadband light beam in the wavelength range of 390 to 700 nm. Convex lenses 208, 210 reduce the angle of divergence of light from the two LEDs 202, 204 so that light can be effectively coupled into the filter cube 108.

Multiband filters have been used in fluorescence microscopy as well as fluorescence in-situ hybridisation (FISH) applications, but have not been implemented in a real-time PCR setting prior to the present embodiment. Use of multiband filters pose specific challenges such as (i) difficulty in resolving a relative fluorescence unit (RFU) of each fluorophore component from a homogeneous mixture of two or more fluorescence-based DNA probes hybridized to respective DNA targets in a PCR solution, (ii) the CCD favoring a spectral bandwidth of 500 to 550 nm with a tapering of sensitivity for wavelengths below 450 nm and above 600 nm, (iii) a potential for two or more fluorophores to be excited due to a single excitation bandwidth since all fluorophores are excited simultaneously and the corresponding emission spectra are collected simultaneously, and (iv) significant spectral overlap between two (or more) fluorophores such that mixtures of these fluorophores may be difficult to resolve.

Figure 3:
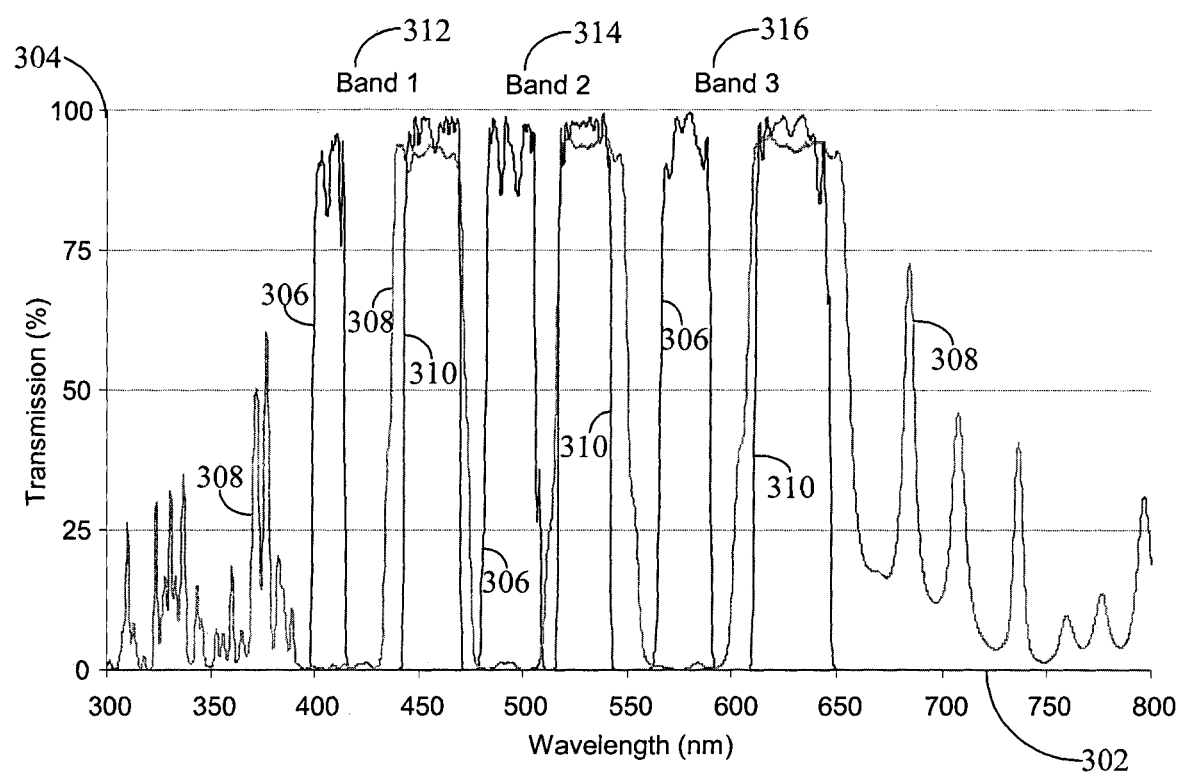
FIG. 3 illustrates a graph of an excitation spectrum and an emission spectrum for the PCR system of FIG. 1 in accordance with the present embodiment.

These challenges are addressed and advantageously overcome by the present embodiment. Referring to FIG. 3, a graph 300 of an excitation spectrum and an emission spectrum for the PCR system 100 in accordance with the present embodiment is depicted. Light wavelength is plotted along the x-axis 302 and percent transmission is plotted along the y-axis 304. The broadband UV-visible light produces the transmission spectrum 306 after passing through the excitation filter 104. This spectrum 306 is also known as an excitation spectrum 306 and is reflected by the dichroic mirror 109 since it does not overlap with the transmission spectrum of the mirror 308. The excitation spectrum 306 is incident on the DNA sample in the imaging chamber 116 and the fluorophores of interest will emit an emission spectrum 310. The emission spectrum 310 will be transmitted through the dichroic mirror 109 to the CCD camera 102 since it is completely contained within the transmission spectrum 308 of the mirror 109. Thus, the multiband filter set comprised of compatible tri-band filters 104, 106, 108 for excitation, emission and dichroic purposes detects each of Band One 312, Band Two 314 and Band Three 316, the bands 312, 314, 316 matched to a specific fluorophore of interest. In accordance with the present embodiment, the tri-band filters 104, 106, 108 are advantageously selected to limit multiplexing to three colors for optimal fluorophore emission differentiation as spectral overlap prevalent in higher order multiband filters prevents accurate resolution of fluorophore components in a real-time PCR system.

Figure 4:
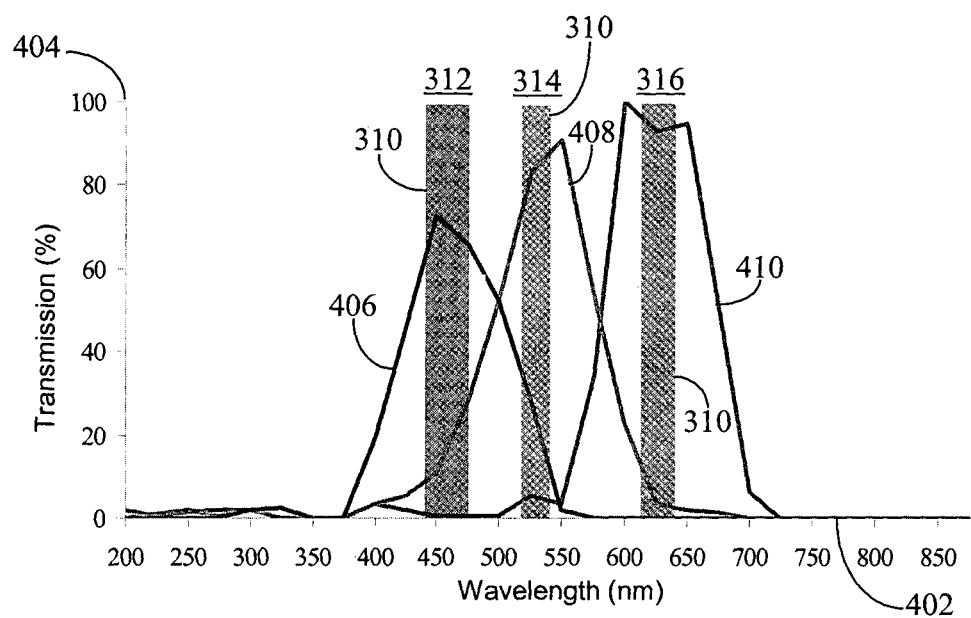
FIG. 4 illustrates a graph of a red, green and blue (RGB) multiband emission spectrum and a RGB response of a color charge-coupled device (CCD) camera of the PCR system of FIG. 1 in accordance with the present embodiment.

Furthermore, the emission spectrum 310 of the tri-band filter overlaps with the peak spectral responses of the red, green and blue channels in the RGB CCD camera 102 as shown in FIG. 4. A graph 400 illustrates the red, green and blue (RGB) multiband emission spectrum 310 and a RGB response of the CCD camera 102. Light wavelength is plotted along the x-axis 402 and percent transmission is plotted along the y-axis 404. The blue 312, green 314 and red 316 components of the multiband emission spectrum 310 are potted along with a blue channel response 406, a green channel response 408 and a red channel response 410 of the color CCD camera 102. It can be observed from the graph 400 that the peak responses of the blue 406, green 408 and red 410 channels approximates the blue 312, green 314 and red 316 components of the multiband emission spectrum 310. The blue component 312 overlaps primarily with the blue channel response 406 of the camera 102, whereas the green component 314 overlaps mainly with the green channel response 408, and the red component 316 overlaps mainly with the red channel response 410.

Figure 5:
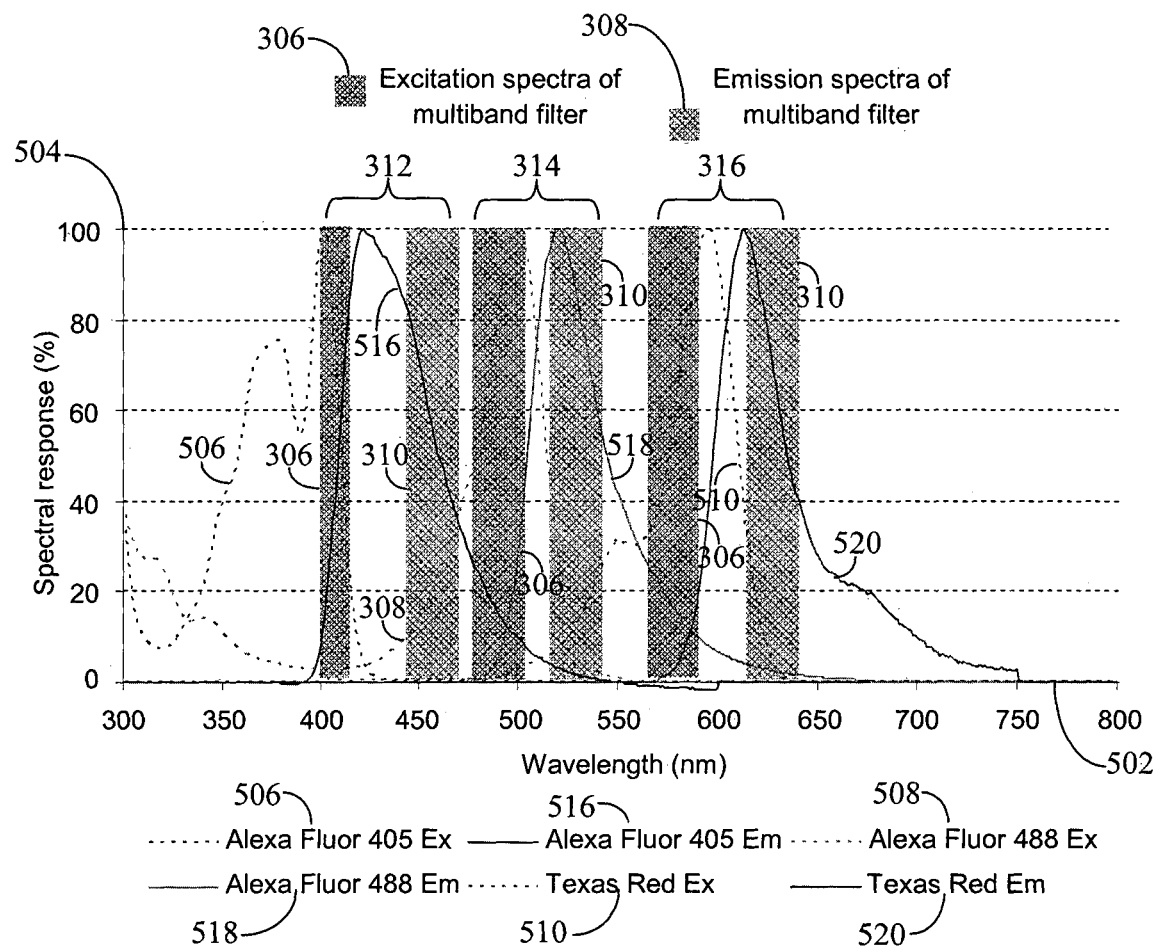
FIG. 5 illustrates a graph of an excitation spectra and an emission spectra of a multiband filter and excitation spectra and emission spectra of fluorophores of the PCR system of FIG. 1 in accordance with the present embodiment.

Thus, in accordance with the present embodiment each multiband component 312, 314, 316 is spectrally distinct and the three fluorophore-conjugated DNA probes are selected such that (a) the peak emission profiles of the fluorophores correspond to both the peak RGB channel responses of the CCD camera and the bandwidths of the tri-band emission filter, and (b) the peak excitation profiles of the fluorophores correspond to the bandwidths of the tri-band excitation filter. Referring to FIG. 5, a graph 500 illustrates the excitation spectra 306 and the emission spectra 310 of the multiband filters 104, 106, 108 and excitation spectra 506, 508, 510 and emission spectra 516, 518, 520 of fluorophores selected for optimal operation in the PCR system 100. The light wavelength is plotted along the x-axis 502 and the percent transmission is plotted along the y-axis 504.

It can be seen from the graph 500 that the excitation spectra 506, 508, 510 of the selected fluorophores should not overlap one another and the emission spectra 516, 518, 520 of the fluorophores should only minimally overlap with one another. Further, the excitation spectra 306 of the multiband filter set 104, 106, 108 should correspond to the peak excitation responses 506, 508, 510 of the fluorophores and the emission spectra 310 of the multiband filter set 506, 508, 510 should cover the peak emission spectra values 516, 518, 520 of the fluorophores.

In accordance with the present embodiment, the selected fluorophores are preferably an Alexa 405-Probe1 Seq.-Dabcy1 probe with the excitation spectra 506 and the emission spectra 516, an Alexa 488-Probe2 Seq.-BHQ1 probe with the excitation spectra 508 and the emission spectra 518, and a Texas Red-Probe3 Seq.-BHQ2 probe with the excitation spectra 510 and the emission spectra 520. Other fluorophores that also meet the criteria of the present embodiment and may potentially be used include Cascade Blue and Pacific Blue (in place of the Alexa 405), FAM and FITC (in place of the Alexa 488) and Cy5 and Alexa 647 (in place of the Texas Red).

Figure 6A:
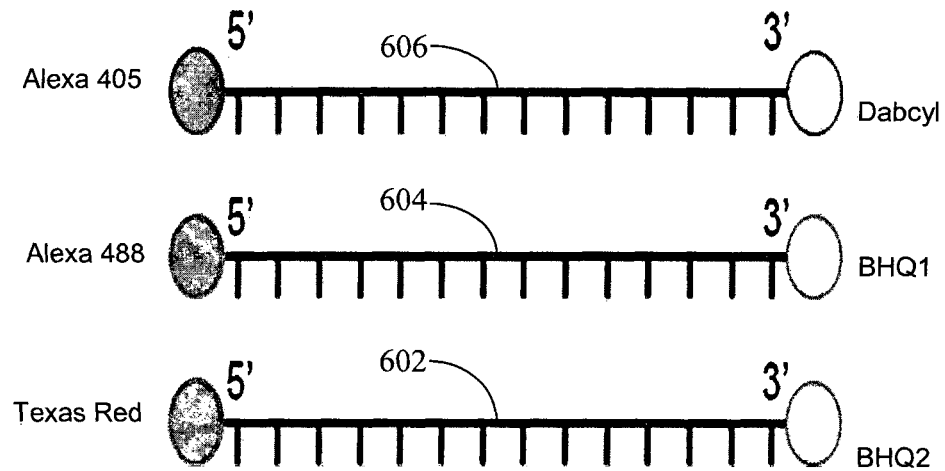
Figure 6B:
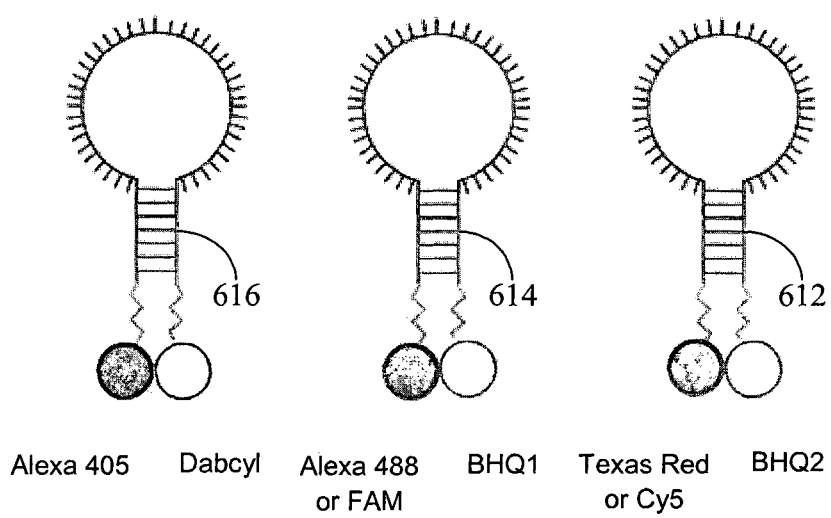

The fluorophores Texas Red or Cy5, Alexa 488 or FAM and Alexa 405 are collectively referred to as RGB fluorophores since they emit red, green and blue fluorescence, respectively, in response to UV-visible broadband light excitation. Referring to FIG. 6, the fluorophores Texas Red or Cy5 602, 612, Alexa 488 or FAM 604, 614 and Alexa 405 606, 616 are depicted. FIG. 6A illustrates the RGB fluorophores 602, 604, 606 in a linear probe configuration and FIG. 6B illustrates the RGB fluorophores 612, 614, 616 in a hairpin probe configuration.

The emission intensity of a fluorophore is defined by the Beer-Lambert Law as follows:

$$I_{em} = k\phi I_{ex}(1-e^{-\varepsilon bc}) \quad (1)$$

where $I_{em}$ is the intensity of the emission light, k is a geometric instrumental factor, $\phi$ is the fluorescence quantum yield, $I_{ex}$ is the intensity of the excitation light, $\varepsilon$ is the molar extinction coefficient, b is the optical path length (distance that light travels through the material), c is the fluorophore concentration. Equation 1 can be approximated by Equation 2 if $\varepsilon bc \leq 0.05$, where b=1 cm:

$$I_{em} = k\phi I_{ex} \varepsilon bc \quad (2)$$

Given that the extinction coefficients of Alexa 405, Alexa 488 and Texas Red are 34,000, 71,000 and 85,000 $M^{-1}$ $cm^{-1}$, respectively, all three fluorophores satisfy the $\varepsilon bc \leq 0.05$ requirement for the approximation in Equation 2 since the maximum concentration of non-quenched fluorophores in a PCR reaction is fixed at 200 nM. Equation 2 can be expressed in matrix notation as follows.

$$\begin{bmatrix} I_{em}^{r1} & I_{em}^{g1} & I_{em}^{b1} \\ \vdots & \ddots & \vdots \\ I_{em}^{m} & I_{em}^{m} & I_{em}^{m} \end{bmatrix} = \quad (3)$$

$$\begin{bmatrix} c_1^{Alx405} & c_1^{Alx488} & c_1^{TxsRed} \\ \vdots & \ddots & \vdots \\ c_n^{Alx405} & c_n^{Alx488} & c_n^{TxsRed} \end{bmatrix} \begin{bmatrix} Q_r^{Alx405} & Q_g^{Alx405} & Q_b^{Alx405} \\ Q_r^{Alx488} & Q_g^{Alx488} & Q_b^{Alx488} \\ Q_r^{TxsRed} & Q_g^{TxsRed} & Q_b^{TxsRed} \end{bmatrix}$$

Equation 3 can be simplified as follows, $$I_{train} = C_{train}Q, \text{ where} \quad (4)$$

$$I = \begin{bmatrix} I_{em}^{r1} & I_{em}^{g1} & I_{em}^{b1} \\ \vdots & \ddots & \vdots \\ I_{em}^{rm} & I_{em}^{gm} & I_{em}^{bm} \end{bmatrix} \quad (5)$$

$$C = \begin{bmatrix} c_1^{Alx405} & c_1^{Alx488} & c_1^{TxsRed} \\ \vdots & \ddots & \vdots \\ c_n^{Alx405} & c_n^{Alx488} & c_n^{TxsRed} \end{bmatrix} \text{ and} \quad (6)$$

$$Q = \begin{bmatrix} Q_r^{Alx405} & Q_g^{Alx405} & Q_b^{Alx405} \\ Q_r^{Alx488} & Q_g^{Alx488} & Q_b^{Alx488} \\ Q_r^{TxsRed} & Q_g^{TxsRed} & Q_b^{TxsRed} \end{bmatrix} \quad (7)$$

As those skilled in the art will understand, the algorithm is divided into a training and a testing phase, whereby matrix Q is determined during the training phase by implementing a non-negative matrix factorization (NMF) algorithm and where the entries of all three matrices are non-negative. This is done by capturing fluorescence images of single fluorophore solutions at known concentrations $C_{train}$, where $I_{train}$ would represent a matrix of n RGB pixels from the region of interest.

In the testing phase, the matrix C is determined as follows, $$C_{test} = I_{test}Q^{-1} \quad (8)$$

where $I_{test}$ represents a new set of n RGB pixels.

FIG. 7, comprising FIGS. 7A, 7B and 7C, illustrates a light insulator 702 of the PCR system 100 in accordance with the present embodiment. Referring to FIGS. 7A and 7B, a front planar schematic view 700 and a top planar schematic view 710 illustrate the conically-shaped light insulator 702. The purpose of the light insulator 702 is to prevent stray light from leaking into the optical detection system as shown in FIG. 7C. FIG. 7C illustrates an optical system 720 of the PCR system 100 incorporating the light insulator 702. In addition to preventing stray light from leaking into the optical detection system 720, the conically-shaped insulator 702 enables the optical system 720, incorporating the camera 102, the multiband filter cube 108 and the light source 110, to be directly mounted onto it via, for example, a C-mount interface.

In regards to the insulator 702, the choice of substrate material is essential to operation of the PCR system 100. It is critical that the internal surfaces of the insulator 702 enhances rather than suppresses the signal-to-noise ratio (SNR) of the fluorescence read-out from the PCR reaction. FIG. 8, comprising FIGS. 8A, 8B, 8C, 8D and 8E, illustrates a comparison of the SNR of the fluorescence read-out in accordance with the present embodiment of a multi-well DNA chip loaded with a FAM probe placed on a glossy black surfaced substrate material and the multi-well DNA chip placed on a reflective aluminum sheet substrate material. Referring to FIGS. 8A and 8B, a view 800 depicts the FAM probe in a multi-well DNA chip placed on a glossy black surface and a view 810 depicts a similar FAM probe in a multi-well DNA chip placed on an aluminum sheet. FIG. 8C depicts a graph 820 of the SNR of fluorescence read-out from each well in the DNA chip where the well numbers are plotted along the x-axis 822 and the SNR is plotted along the y-axis. As can be seen from the graph 820, the SNR 826 of the fluorescence read-out from the wells in the DNA chip placed on the glossy black surface is higher for each well than the SNR 828 of the fluorescence read-out from the wells in the DNA chip placed on the aluminum sheet.

While the aluminum sheet substrate produces lower SNR in the fluorescence read-out from the wells in the DNA chip, the reflectivity of the aluminum sheet can be problematic. For example, the aluminum sheet reflects blue light under UV excitation thereby suppressing actual blue emissions from UV probe DAPI samples as shown in FIGS. 8D and 8E. FIG. 8D depicts a view 830 of serial dilutions of a UV probe in PCR reaction tubes 832 placed on a glossy black surface and FIG. 8E depicts a view 840 of a UV probe in PCR reaction tubes 842 placed on an aluminum sheet. Thus, in accordance with the present embodiment, the light insulator 702 is made from black anodized aluminum in order to give the aluminum a glossy black finish, thereby achieving the SNR reduction of the aluminum material without the drawbacks of reflective aluminum.

FIG. 9, comprising FIGS. 9A, 9B, 9C, 9D and 9E, illustrates a correlation between fluorescence read-out of a conventional real-time PCR system and the real-time PCR system 100 in accordance with the present embodiment. Referring to FIG. 9A, a view 900 depicts the end-point fluorescence read-outs 902, 904 of a FAM fluorophore as measured in two identical reactions after an amplification of a mouse glyceraldehyde 3-phosphate dehydrogenase (GAPDH) specific target for thirty-five cycles. Likewise, in FIG. 9B, a view 910 depicts the end-point fluorescence read-outs 912, 914 of a FAM fluorophore as also measured in two identical reactions after an amplification of a mouse GAPDH-specific target for twenty-five cycles.

FIG. 9C depicts a graph 920 of corresponding PCR amplification results using a conventional real-time PCR system and the real-time PCR system 100, where the cycle number is plotted along the x-axis 922 and the relative fluorescence units (RFUs) are plotted along the y-axis 924. In both cases (twenty-five cycles 930, 932 and thirty-five cycles 926, 928), the results are compared against the end-point RFU values of the same reactions using a conventional non-portable real-time PCR system. FIG. 9D depicts a bar graph 940 of normalized fluorescence (plotted along the y-axis 942) read-out of the PCR system 100 944, 945 and the conventional PCR system 946, 947 correlated after twenty-five cycles, and FIG. 9E depicts a bar graph 950 of normalized fluorescence (plotted along the y-axis 952) read-out of the PCR system 100 954, 955 and the conventional PCR system 956, 957 correlated after thirty-five cycles. Thus, it can be seen from FIG. 9 that the portable real-time PCR system 100 provides similar detection sensitivity as conventional PCR systems which are not portable.

Figure 10A:
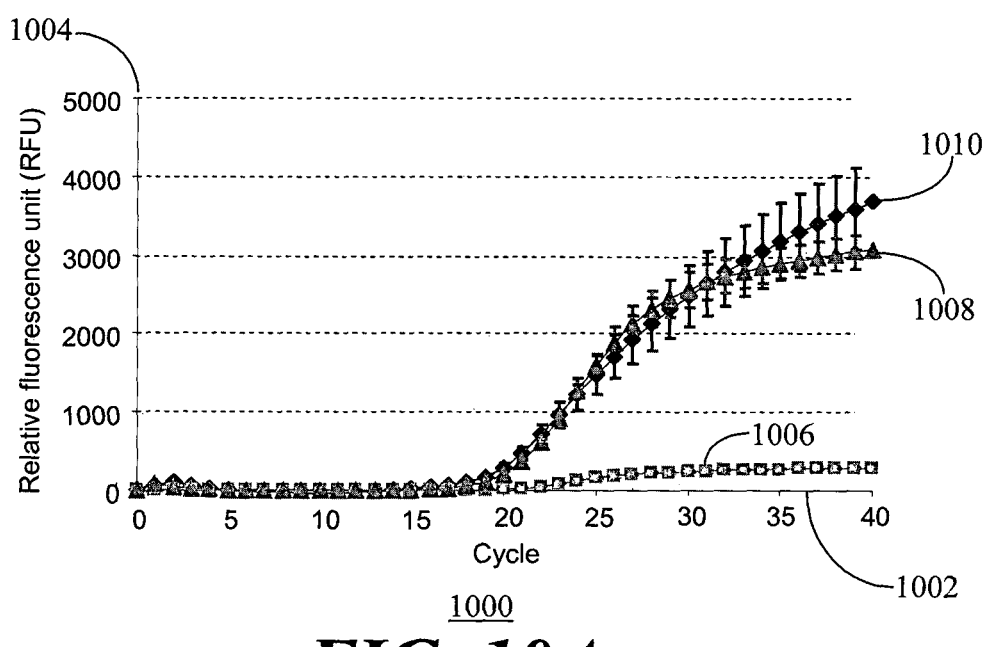

FIG. 10, comprising FIGS. 10A, 10B, 10C and 10D, illustrates resolution of Cy3 and Cy5 fluorescence in a PCR solution using a conventional PCR system and the PCR system 100 in accordance with the present embodiment. Referring to FIG. 10A, a graph 1000 having cycles plotted along the x-axis 1002 and RFU plotted along the y-axis 1004 illustrates triplex real-time PCR amplification results of GAPDH, β-actin and beta-2 microglubulin (B2M) mouse control genes using Cy3-conjugated DNA probes 1006, Cy5-conjugated DNA probes 1008, and FAM-conjugated DNA probes 1010 with the conventional PCR system. The amplification of the Cy3-β-actin 1006 appears low since the conventional PCR system is not optimized for detecting Cy3.

Figure 10B:
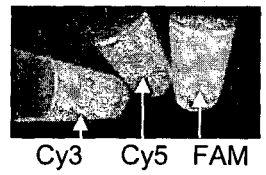
Figure 10C:
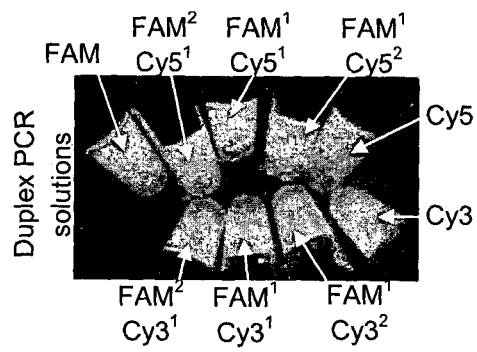
Figure 10D:
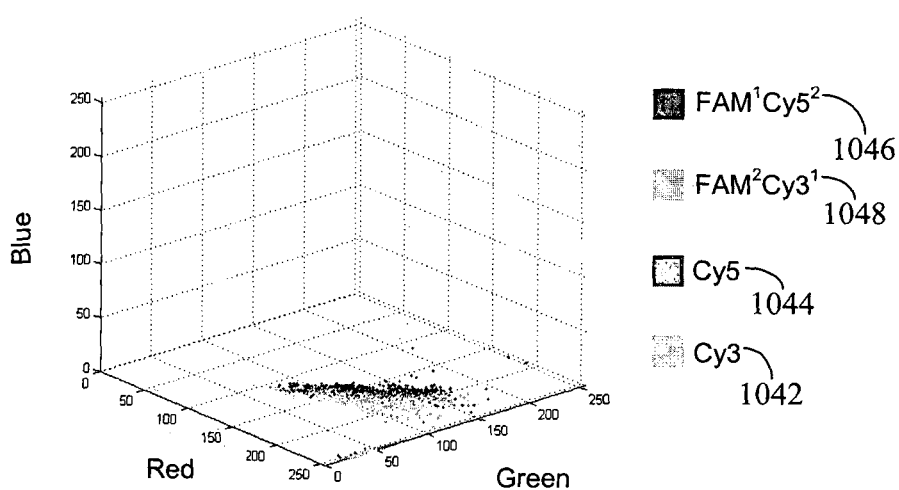

Referring to FIGS. 10B and 10C, a view 1020 (FIG. 10B) depicts end-point singleplex amplification results of FAM-GAPDH, Cy3-β-actin and Cy5-B2M in the conventional PCR system and a view 1030 (FIG. 10C) depicts end-point duplex amplification results where $Probe_1^x Probe_2^y$ represents x parts of $Probe_1$ and y parts of $Probe_2$ in a duplex solution in the conventional PCR system. The end-point fluorescence read-out of the singleplex amplification for Cy3-β-actin, as measured from the proposed optical system, is comparable to FAM-GAPDH and Cy5-B2M, as shown in the view 1020. The duplex PCR reactions in the view 1030 highlights the difficulty in resolving Cy3 and Cy5 where $FAM^2 Cy3^1$ and $FAM^1 Cy5^2$ have a similar color profile, and this is observed in FIG. 10D where a three-dimensional RGB scatter plot 1040 shows significant spectral overlap of Cy3 1042 and Cy5 1044 as well as $FAM^1 Cy5^2$ 1046 and $FAM^2 Cy3^1$ 1048.

Figure 11:
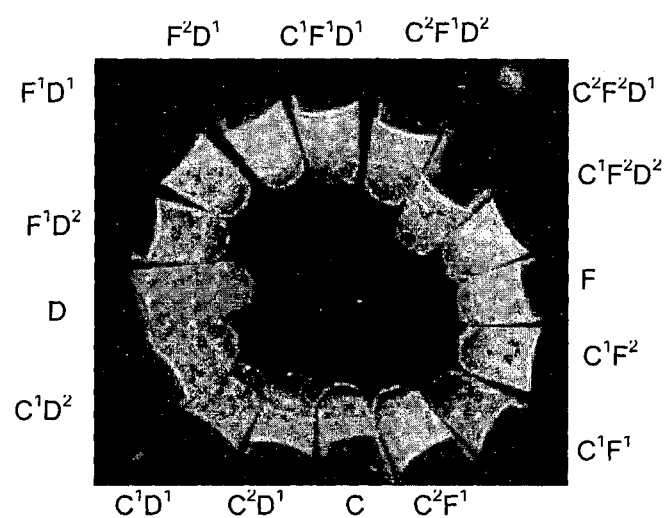
FIG. 11 illustrates single-plex, duplex and triplex mixtures of spectrally different fluorophores in the PCR system of FIG. 1 in accordance with the present embodiment.

FIG. 11 depicts a view 1100 illustrating singleplex, duplex and triplex mixtures of spectrally different fluorophores in the PCR system 100 in accordance with the present embodiment, where $C^x F^y D^z$ denotes x parts of Cy3, y parts of FAM and z parts of DAPI, respectively. The view 1100 shows a broader spectrum of singleplex, duplex and triplex mixtures in the PCR solution where 'magenta', 'cyan' and 'yellow' indicate a mixture between Cy3 and DAPI ($C^1 D^1$), a mixture of FAM and DAPI ($F^1 D^1$), and a mixture of Cy3 and FAM ($C^1 F^1$), respectively. An equal amount of all three fluorophores ($C^1 F^1 D^1$) results in 'white fluorescence'.

Figure 12A:
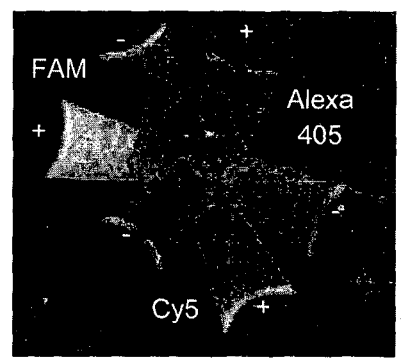
Figure 12B:
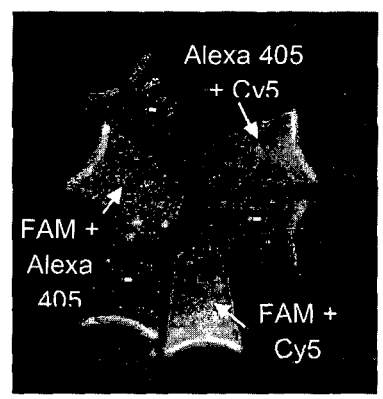

Given the spectral overlap between Cy3 and Cy5, fluorescein amidite Bull-Hutchings-Quayle One (FAM-BHQ1), Cy5-BHQ2 and Alexa 405-Dabcy1 were selected as the set of probes for use with the PCR system 100 where Cy5 is chosen over Cy3 due to the better spectral separation of Cy5 from FAM and Alexa 405, as compared to Cy3. FIG. 12, comprising FIGS. 12A and 12B, illustrates end-point PCR amplification results of GAPDH, B2M and β-actin mouse control genes using the selected FAM, Cy5 and Alexa 405 probes. Referring to FIG. 12A, a view 1200 depicts singleplex reactions of FAM, Cy5 and Alexa 405 and, referring to FIG. 12B, a view 1220 depicts duplex reactions of FAM+ Alexa 405, FAM+Cy5 and Alexa 405+Cy5. The background fluorescence of Alexa 405 appears to be higher than that of FAM and Cy5. However, the background fluorescence of Alexa 405 can be reduced by implementing Alexa 405 in the hairpin probe configuration 616 (FIG. 6B) so that Dabcy1 can more effectively quench the fluorescence in a non-hybridized state due to its proximity to the fluorophore.

Figure 13:
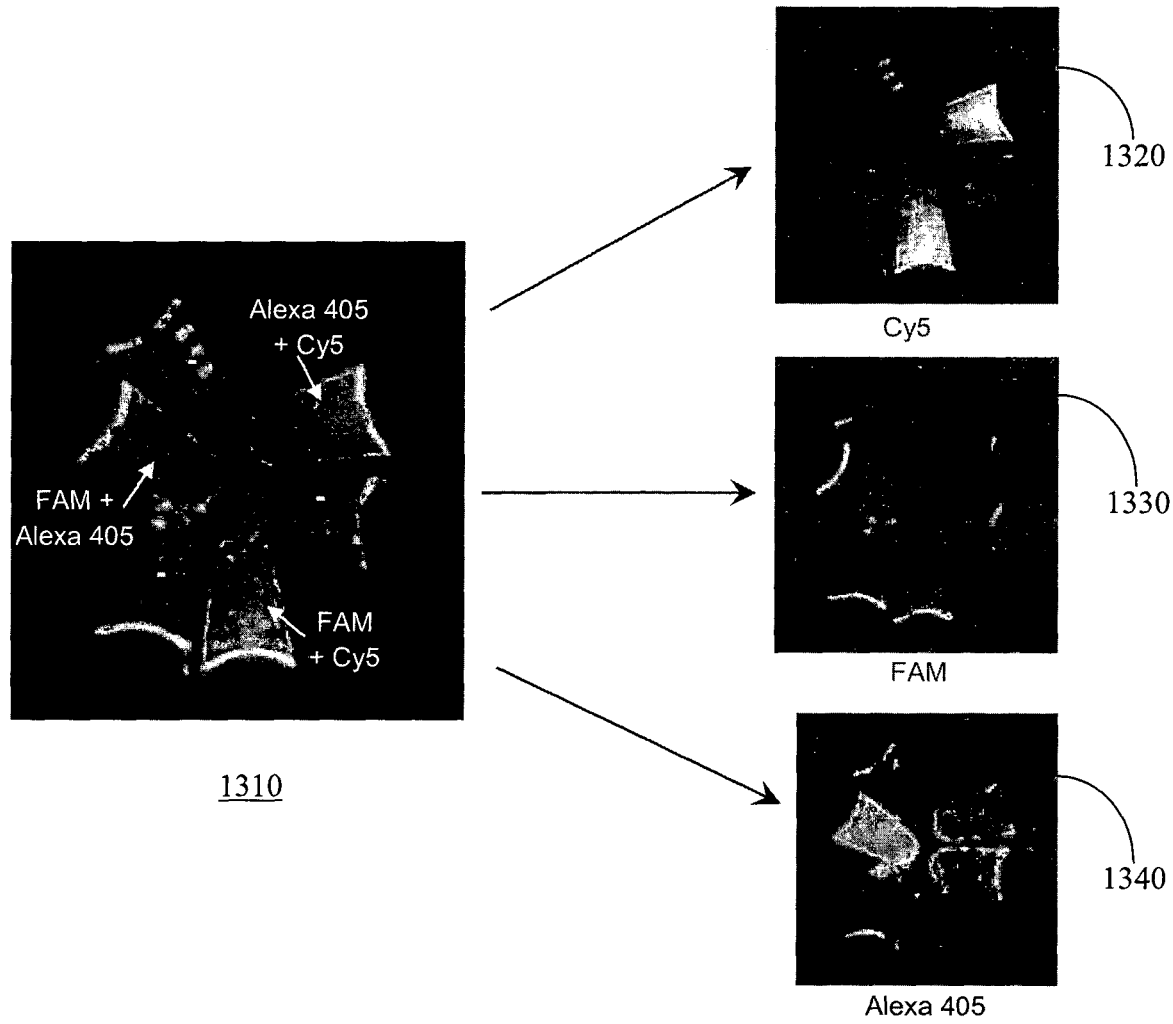
FIG. 13 illustrates color-based deconvolution for resolving multiplexed PCR solutions into their fluorophore components utilizing the PCR system of FIG. 1 in accordance with the present embodiment.

Referring next to FIG. 13, an illustration 1300 depicts color-based deconvolution for resolving multiplexed PCR solutions into their fluorophore components utilizing the PCR system 100 in accordance with the present embodiment. Duplex reactions of FAM+Alexa 405, FAM+Cy5 and Alexa 405+Cy5 as depicted in a view 1310 are resolved into Cy5, FAM and Alexa 405 fluorophore components 1320, 1330, 1340 using the color-based deconvolution algorithm of Equations 1 to 8, above.

Thus, it can be seen that a portable real-time PCR system 100 which overcomes the drawbacks of prior art systems and provides a system with (i) non-movable components, (ii) a small footprint, (iii) battery operation, (iv) sufficient detection sensitivity, and (v) moderate throughput and multiplexing. The portable real-time PCR system 100 in accordance with the present embodiment includes an optical system that incorporates the RGB color CCD camera 102, the full multiband filter system including the filters 104, 106 and the filter cube 108 with the dichroic mirror 109, the RGB fluorescence probes, the UV-visible light source 110, the light-tight imaging chamber 116, and the color-based deconvolution algorithm (Equations 1 to 8) enabled by the computer 118.

The key advantageous features of the PCR system 100 include: (i) it is non-motorized, and therefore can be incorporated into point-of-care diagnostic devices that require a fluorescence read-out, (ii) it enables both real-time and end-point quantification of fluorophores in a multiplexed reaction via the deconvolution program, and (iii) it allows for optical multiplexing up to three targets as well as spatial multiplexing since the CCD camera and focus lens in the setup retain spatial information. In order to achieve optimal performance, the multiband filters 104, 106, 108 need to have spectral properties that match both the spectral properties of the fluorescence probes employed and the peak spectral responses of the RGB camera 102. For example, the excitation and emission bandwidths of the multiband filters 104, 106, 108 corresponding to the Alexa 405 and Texas Red probes can be customized to be broader since the CCD sensitivity of the RGB camera 102 is generally poorer for these probes as compared to Alexa 488. In a laboratory setup, the UV-visible light source 110 is ideally implemented using a mercury/xenon lamp, but for a portable outdoor setup, a compact light source 110 combining UV and visible white LEDs as shown in the light source arrangement 200 would be preferred.

In addition to real-time and end-point PCR detection, the use of the PCR system 100 can be extended to other application domains such as DNA microarray, fluorescence-based enzyme-linked immunosorbent assay (ELISA) and live/dead staining systems. The optical system 720 can be implemented as part of an integrated device that implements one or more of these assays, or alternatively, it can be a stand-alone fluorescence reader similar to a gel documentation device, except that it provides highly specific and multiplexed fluorescence read-out.

Although the system 100 is designed to detect the Alexa 405, Alexa 488 and Texas Red fluorophores, other fluorophores that meet the required spectral properties of the multiband filter and camera can potentially be used, for example, Cascade Blue and Pacific Blue (in place of Alexa 405), FAM and FITC (in place of Alexa 488), and Alexa 647 and Cy5 (in place of Texas Red). The probes can be in a linear or hairpin configuration (see FIGS. 6A and B, respectively). In addition, the optical system 720 can also be used to read fluorescence from other common dyes, such as SYBR Green, DAPI and propidium iodide.

Color deconvolution has been traditionally used in histology for resolving absorbance-based dyes, such as hematoxylin, eosin and DAB, from images acquired using a light microscope. In the PCR system 100, color deconvolution is advantageously adapted for fluorescence images where the emphasis is on the relationship between fluorescence emission vs. concentration of the fluorophores, rather than transmitted light vs. dye concentration in conventional PCR systems. The deconvolution algorithm including Equations 1 to 8 is based on the NMF approach, which is clearly more intuitive than the standard linear deconvolution methods used by many conventional PCR systems since NMF works under the constraint that each fluorophore contributes non-negatively to the overall fluorescence intensity. Also, NMF is more efficient in detecting low fluorescence signals as compared to the conventional approach.

NMF has been previously used for blind color deconvolution of up to a maximum of two stains in histology images, but, in accordance with the present embodiment, fluorescence images need to be deconvoluted into three fluorophore components. Hence, the NMF deconvolution algorithm has been advantageously modified such that training and testing phases are introduced whereby NMF is used in the training phase to determine the deconvolution matrix (Equations 5 to 7), after which the matrix is used in the testing phase to quantify the fluorophore components. As compared to linear color deconvolution, NMF is algorithmically more complex and iterative. However, the NMF version employed in the PCR system 100 in accordance with the present embodiment has been advantageously modified so that convergence is achieved and the number of iterations is minimized. While exemplary embodiments have been presented in the foregoing detailed description of the invention, it should be appreciated that a vast number of variations exist.

It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of elements and method of operation described in an exemplary embodiment without departing from the scope of the invention as set forth in the appended claims.

What is claimed is:

1. A multiplexed polymerase chain reaction (PCR) DNA detection system comprising:
   fluorophore-quencher probes, the fluorophore-quencher probes comprising:
      a first fluorophore-quencher probe which emits red light;
      a second fluorophore-quencher probe which emits green light; and
      a third fluorophore-quencher probe which emits blue light;
   a light-tight imaging chamber comprising a light insulator;
   a light source configured to provide excitation light to the light-tight imaging chamber;
   a triple bandpass emission filter color charge-coupled device (CCD) system configured to cover a predetermined field of view within the light-tight imaging chamber, the triple bandpass emission filter color CCD system comprising a color CCD camera and a triple bandpass emission optical filtering device optically coupled between the color CCD camera and the light-tight imaging chamber;
   a computing device coupled to the CCD camera and configured to resolve fluorescence from a DNA sample in the light-tight imaging chamber into its fluorophore components by performing a color-based deconvolution method on image pixels captured by the CCD camera of non-quenched fluorophore excitation emissions from the imaging chamber, the color-based deconvolution method comprising calculating a matrix C of fluorescence excitation of the DNA sample within the field of view of the color CCD camera using the non-negative matrix factorization (NMF) equation:

$$C_{test} = I_{test} Q^{-1}$$

wherein $I_{test}$ is a matrix of red, green and blue intensity of the image pixels captured by the color CCD camera of the non-quenched fluorophore excitation emissions and Q is a matrix derived in response to using the system for a plurality of training and testing phases of multiplexed PCR reactions using predetermined targets, wherein the light insulator is configured to enhance a signal-to-noise ratio of the fluorescence from the DNA sample in the light-tight imaging chamber.

2. The multiplexed PCR DNA detection system in accordance with claim 1 wherein the triple bandpass emission optical filtering device comprises triple bandpass excitation, emission and dichroic filters.

3. The multiplexed PCR DNA detection system in accordance with claim 2 wherein the first, second and third fluorophore-quencher probes are selected further in response to the emission profiles of the fluorophores corresponding to each of the three bandwidths of the triple bandpass emission optical filtering device.

4. The multiplexed PCR DNA detection system in accordance with claim 1 wherein the light source comprises a light emitting diode (LED) light source.

5. The multiplexed PCR DNA detection system in accordance with claim 4 wherein the light source comprises a battery-operated LED light source.

6. The multiplexed PCR DNA detection system in accordance with claim 1 wherein the first, second and third fluorophore-quencher probes quench respective first, second and third fluorophores corresponding to peak channel responses of the color CCD camera such that emission profiles of the first, second and third fluorophores substantially match red, green and blue peak channel responses of the color CCD camera.

7. The multiplexed PCR DNA detection system in accordance with claim 6
   wherein $I_{test}$ is a matrix of red, green and blue intensity of the image pixels captured by the CCD camera corresponding to the resolved fluorescence from the DNA sample.

8. The multiplexed PCR DNA detection system in accordance with claim 1 wherein the light insulator comprises black anodized aluminium.

9. The multiplexed PCR DNA detection system in accordance with claim 1 further comprising one or more lenses optically coupled to the color CCD camera to define the predetermined field of view within the light-tight imaging chamber.

10. A multiplexed polymerase chain reaction (PCR) DNA detection system comprising:
    three fluorophore-quencher probes, the fluorophore-quencher probes comprising:
       a first fluorophore-quencher probe which emits red light;
       a second fluorophore-quencher probe which emits green light; and
       a third fluorophore-quencher probe which emits blue light;
    a light emitting diode (LED) light source;
    a light-tight imaging chamber configured to enclose the light source, a DNA sample and the three fluorophore-quencher probes, wherein the imaging chamber comprises a light insulator comprising black anodized aluminum;
    a triple bandpass emission filter color charge-coupled device (CCD) system configured to cover a predetermined field of view within the light-tight imaging chamber, the triple bandpass emission filter color CCD system comprising a CCD-based RGB camera and a triple bandpass emission optical filtering device optically coupled between the CCD-based RGB camera and the predetermined field of view within the light-tight imaging chamber; and
    a computing device coupled to the CCD-based RGB camera and configured to resolve fluorescence from the DNA sample in the light-tight imaging chamber into its fluorophore components by the computing device performing a color-based deconvolution method on image pixels captured by the CCD-based RGB camera of non-quenched fluorophore excitation emissions from the imaging chamber, the color-based deconvolution method comprising calculating a matrix C of fluorescence excitation of the DNA sample within the field of view of the CCD-based RGB camera using the non-negative matrix factorization (NMF) equation:

$$C_{test} = I_{test} Q^{-1}$$

wherein $I_{test}$ is a matrix of red, green and blue intensity of the image pixels captured by the CCD-based RGB camera of the non-quenched fluorophore excitation emissions and Q is a matrix derived in response to using the system for a plurality of training and testing phases of multiplexed PCR reactions using predetermined targets.

11. A multiplexed polymerase chain reaction (PCR) DNA detection system comprising:
three fluorophore-quencher probes comprising:
a first fluorophore-quencher probe which emits red light and is selected from the group comprising Texas Red, Cy5 and Alexa 647 red emission profile fluorophore-quencher probes;
a second fluorophore-quencher probe which emits green light and is selected from the group comprising Alexa 488, fluorescein amidite (FAM) and fluorescein isothyocyanate (FITC) green emission profile fluorophore-quencher probes; and
a third fluorophore-quencher probe which emits blue light and is selected from the group comprising Alexa 405, Cascade Blue or Pacific Blue blue emission profile fluorophore-quencher probes;
a battery-operated light emitting diode (LED) light source;
a light-tight imaging chamber configured to enclose the light source, a DNA sample and the three fluorophore-quencher probes, wherein the imaging chamber comprises a black anodized aluminium light insulator;
a triple bandpass emission filter color charge-coupled device (CCD) system optically coupled to the light-tight imaging chamber, the triple bandpass emission filter color CCD system comprising a CCD-based RGB camera and a lens optically coupled to the CCD-based RGB camera and configured to define a predetermined field of view of the CCD-based RGB camera within the light-tight imaging chamber, the triple bandpass emission filter color CCD system further comprising a triple bandpass emission optical filtering device optically coupled between the CCD-based RGB camera and the predetermined field of view within the light-tight imaging chamber; and
a computing device coupled to the CCD-based RGB camera and configured to implement a color-based deconvolution method on image pixels captured by the CCD-based RGB camera, the color-based deconvolution method comprising calculating a matrix C of fluorescence excitation of the DNA sample within the field of view of the CCD-based RGB camera using the non-negative matrix factorization (NMF) equation:

$$C_{test} = I_{test} Q^{-1}$$

wherein $I_{test}$ is a matrix of red, green and blue intensity of the image pixels captured by the CCD-based RGB camera of the non-quenched fluorophore excitation emissions and Q is a matrix derived in response to using the system for a plurality of training and testing phases of multiplexed PCR reactions using predetermined targets, each of the plurality of training and testing phases using a single fluorophore solution of a predetermined target at a known concentration and using the NMF equation:

$$I_{train} = C_{train} Q$$

wherein $C_{train}$ is a matrix of known fluorescence excitation of the single fluorophore solution of the predetermined target at the known concentration and $I_{train}$ is a matrix of intensity of the image pixels captured within the field of view of the CCD-based RGB camera during the training and testing phase.

* * * * *